United States Patent
Gillick et al.

(10) Patent No.: US 8,429,831 B2
(45) Date of Patent: Apr. 30, 2013

(54) DRUG-ELUTING COATINGS APPLIED TO MEDICAL DEVICES BY SPRAYING AND DRYING TO REMOVE SOLVENT

(75) Inventors: Matthew J. Gillick, Murrieta, CA (US); John E. Papp, Temecula, CA (US); Kevin Seiki, Murrieta, CA (US); Hung T. Nguyen, San Diego, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 893 days.

(21) Appl. No.: 12/554,820

(22) Filed: Sep. 4, 2009

(65) Prior Publication Data

US 2011/0059228 A1   Mar. 10, 2011

(51) Int. Cl.
*F26B 5/06* (2006.01)

(52) U.S. Cl.
USPC ............ 34/78; 34/80; 34/90; 34/210; 62/310; 134/902

(58) Field of Classification Search ...................... 34/380, 34/381, 413, 497, 78, 80, 90, 138, 210; 62/304, 62/310; 134/95.2, 95.3, 153, 902
See application file for complete search history.

(56) References Cited

U.S. PATENT DOCUMENTS

| | | | | |
|---|---|---|---|---|
| 3,290,788 A | * | 12/1966 | Seelandt | 34/294 |
| 3,750,306 A | * | 8/1973 | Rodwin et al. | 34/69 |
| 4,733,665 A | | 3/1988 | Palmaz | |
| 4,800,882 A | | 1/1989 | Gianturco | |
| 4,886,062 A | | 12/1989 | Wiktor | |
| 5,174,045 A | * | 12/1992 | Thompson et al. | 34/58 |
| 5,224,503 A | * | 7/1993 | Thompson et al. | 134/95.2 |
| 5,507,768 A | | 4/1996 | Lau et al. | |
| 5,514,154 A | | 5/1996 | Lau et al. | |
| 5,564,200 A | * | 10/1996 | Strahm | 34/636 |
| 5,569,295 A | | 10/1996 | Lam | |
| 6,293,121 B1 | * | 9/2001 | Labrador | 62/304 |
| 6,357,141 B1 | * | 3/2002 | Kearsley et al. | 34/305 |
| 6,691,720 B2 | * | 2/2004 | Bergman et al. | 134/155 |
| 7,340,846 B1 | | 3/2008 | Jou | |
| 7,572,336 B2 | | 8/2009 | Van Sciver et al. | |
| 2008/0311280 A1 | | 12/2008 | Rego et al. | |
| 2009/0035449 A1 | | 2/2009 | Chen et al. | |
| 2009/0165326 A1 | * | 7/2009 | Hedberg et al. | 34/312 |

(Continued)

FOREIGN PATENT DOCUMENTS

| | | | |
|---|---|---|---|
| DE | 4236478 A1 | * | 5/1994 |
| EP | 761863 A1 | * | 3/1997 |

(Continued)

OTHER PUBLICATIONS

IVEK Precision Liquid Dispensing, Metering & Ceramic Pumps, Product Information, IVEK Corp. 2 pgs (2008).

(Continued)

*Primary Examiner* — Stephen M. Gravini
(74) *Attorney, Agent, or Firm* — Squire Sanders (US) LLP

(57) ABSTRACT

A coating device for coating a medical device with a drug-eluting material uses an in-process drying station between coats to improve a drug release profile. The drying station includes a heat nozzle configured for applying a uniform drying gas. A coating process using the dryer includes a closed-loop control for the gas between drying steps and an improved nozzle for producing more consistent spray patterns.

29 Claims, 9 Drawing Sheets

U.S. PATENT DOCUMENTS

| | | | |
|---|---|---|---|
| 2009/0241998 A1 * | 10/2009 | Kesil et al. | 134/99.2 |
| 2011/0000427 A1 | 1/2011 | Robson et al. | |
| 2012/0167410 A1 * | 7/2012 | Abate et al. | 34/443 |

FOREIGN PATENT DOCUMENTS

| | | | |
|---|---|---|---|
| EP | 884764 A2 * | 12/1998 | |
| FR | 1 238 899 | 8/1960 | |
| GB | 1 024 671 | 3/1966 | |
| GB | 2 384 295 | 7/2003 | |
| JP | 04240307 A * | 8/1992 | |
| JP | 07241452 A * | 9/1995 | |
| WO | WO 2010024701 A2 * | 3/2010 | |

OTHER PUBLICATIONS

Sylvania air heaters, product information 22 pgs (2005).
U.S. Appl. No. 12/497,133, filed Jul. 2, 2009, Bobson et al.
U.S. Appl. No. 12/540,302, filed Aug. 12, 2009, Papp et al.
U.S. Appl. No. 12/554,671, Sep. 4, 2009, Pacetti et al.
International Search Report for PCT/US2010/046851, mailed May 16, 2011, 8 pgs.

* cited by examiner

DRUG-ELUTING COATINGS APPLIED TO MEDICAL DEVICES BY SPRAYING AND DRYING TO REMOVE SOLVENT

BACKGROUND OF THE INVENTION

1. Field of the Invention

The present invention relates to drug-eluting medical devices; more particularly, this invention relates to processes for controlling the interaction among polymer, drug and solvent, and the release rate of a drug for drug eluting medical devices.

2. Background of the Invention

Strict pharmacological and good mechanical integrity of a drug eluting medical device are required to assure a controlled drug release. Significant technical challenges exist when developing an effective and versatile coating for a drug eluting medical device, such as a stent.

A coating may be applied by a spray coating process. A drug-polymer composition dissolved in a solvent is applied to the surface of a medical device using this method. The amount of drug-polymer to be applied has been expressed as a target coating weight, which corresponds to the weight of the coating after a substantial amount of the solvent has been removed.

It is desirable to obtain better control over the drug-eluting product. Specifically, there is a need to better control the rate of release of a drug, or the effectiveness of a drug when released from the coating. To date the known prior art has failed to provide adequate solutions.

SUMMARY OF THE INVENTION

The invention improves on the art by providing an apparatus and method for forming a drug-eluting coating that offers greater control over the release rate for a drug and less undesired interaction between a carrier solvent and the drug-polymer matrix. According to the embodiments, a spray nozzle is used to apply the coating material. And a dryer is used to apply inter-pass drying of coating. The term "inter-pass drying" means drying, or removing solvent between one, two, three or more spray passes. The weight of material per coat is very light, about 5% of the total coating weight according to one embodiment. This means, for this particular embodiment, 20 coats are needed to reach 100% of the coating weight.

Previous efforts to produce a more consistent and stable drug release profile have not been entirely satisfactory. A more precise, controllable/predictable release rate is sought. Efforts to improve upon the controllability and consistency of the release rate of the drug have focused on the structure of the polymer, type or structure of the polymer, and the type of solvent used. However, these improvements have not been able to satisfactorily meet the needs for certain clinical applications, or provide a morphology that can be widely used.

The disclosure includes aspects of both a spraying and drying step during the coating of a medical device. The drying aspect will be discussed first.

A "drug release profile", or "release profile" means the morphology, or characteristics of a drug-eluting matrix that delivers an expected therapeutic behavior after being placed within a body. A drug release profile, or release profile therefore informs one of such things as the predictability of the release rate, variation, if any, in the release rate over time or on a per unit area basis across a drug-eluting surface.

It has been discovered that a significant improvement in the ability to tailor a drug release profile to suit a particular objective such as producing a specific release rate, uniformity in the release rate over a drug eluting surface, and/or uniformity in a production setting (high throughput) lay in obtaining more precise control over the amount of solvent present, or rate of solvent removal. The criticality of solvent removal, distribution, etc. generally depends on the drug-polymer-solvent formulation and particular objectives sought. While it is known that the morphology of a drug-polymer matrix is influenced by the presence of a solvent, it was discovered that this interaction played a more significant role than previously thought. Based on this conclusion, a more effective process for controlling the amount of solvent-polymer-drug interaction was sought. It was found that the coating weight per spray cycle and manner in which solvent was removed, in connection with the coating thickness was an important consideration.

A relatively high coating weight per spray cycle has been sought in the past, because this minimizes process time and increases throughput. Maintaining control over the amount or rate of solvent removal is, however, challenging unless an applied coating layer is relatively thin. If the applied layer is too thick the resistance of the solvent to removal quickly becomes non-linear and therefore more difficult to control or predict. When the solvent is removed from a thick layer, therefore, the potential for undesired interaction among the solvent, polymer and drug, and related problems begin to impair the ability to retain control over the release profile.

The biocompatibility of the polymer used for a drug eluting medical device, e.g., a stent, is essential. The polymer must be non-inflammatory, capable of being expanded without flaking or delaminating from the stent, and be able to control the drug release at a predictable rate. Very few polymer systems can meet the requirements. Preferably, EVAL is chosen as a drug matrix material for drug eluting stents. It has shown favorable biological responses. EVAL is a semi-crystalline random copolymer and it is hygroscopic due to its hydroxyl group. The percentage crystallinity of EVAL coating on the stent is dependent on the process conditions (process temperature, humidity, or residual solvent). A solvent (DMAc or DMSO) used to dissolve EVAL has a high boiling point. As such, the solvent must be actively removed from the coating, e.g., by heating.

Process conditions can affect the desired morphology. For example, if there is excess residual solvent, i.e., solvent not removed between or after a spray cycle, the solvent can induce a plasticizing effect, which can significantly alter the release rate. Therefore, it can be critically important to have a process that produces a coating with consistent properties—crystallinity, % solvent residue, % moisture content, etc. If one or more of these parameters are not properly controlled, such that it varies over the thickness or across a surface of a drug-eluting device, then the release profile is affected. One or more of these considerations can be more critical for some drug-polymer-solvent formulations than for other formulations.

To facilitate the incorporation of a drug on a stent, spraying a low solid percent polymer/drug solution over the stent followed by removing the solvent has become feasible in controlling the amount of drug (in micrograms range) deposited on the stent and the release profile. It has now been discovered that a good coating quality benefits from using this spray technique, i.e., properties such as the crystallinity, % solvent residue, and % moisture content are more controllable as the coating weight is built up over several applied coatings. However, a stent having tight geometry (to minimize the crimped stent OD size) adds significant technical challenges to this method. There is a need to remove at least some of the solvent, in an efficient, predictable manner between spray cycles (a spray cycle may include one or more spray passes, e.g., passing a spray nozzle lengthwise over a rotating stent). In a preferred embodiment, a spray cycle includes one, two, three or more passes in order to obtain a 5% coating weight in a spray cycle. Ideally one would want to remove all solvent after each coating. It will be readily understood, however, that this is not a practical solution. Indeed it may not even be possible for solvents having a relatively high boiling point, such as DMAc. Accordingly, even assuming one could remove all, or substantially all solvent between each spray cycle, the need in the art would not be met because this drying phase would be too time consuming.

Previous studies of the drying effect on drug release (EVAL-drug system) indicated a need for an in-process drying technique to remove a solvent on the coated stent after each spray cycle. This is a critical step in producing more stable products while retaining a high throughput.

The properties of a solvent, e.g., surface tension, vapor pressure or boiling point, viscosity, and dielectric constant, used in dissolving a polymer have a dominant effect on the coating quality, coating process throughput, drug stability, and the equipment required to process it. A solvent can, of course, be removed by applying a heated gas over the stent. Surprisingly and unexpectedly, however, it was found that this drying step must be carefully controlled in order to achieve the desired end result. A uniform and efficient heat transfer from the gas to the coating surface must also take place.

The evaporation rate of a suitable solvent has an inverse relationship with the coating thickness (generally inversely proportional to the thickness) for a thin film coating. And the resistance increases non-linearly as the coating thickness increases. As alluded to earlier, this non-linearity should be avoided. When the thickness is within the linear range higher efficiency, uniformity and more control is achieved when removing the solvent. As a result, a more consistent drug release profile is obtained because there is the least drug-solvent-polymer interaction, solvent plasticizing and extracting of the drug. It is therefore desired to achieve more control over, not only the uniformity of properties across the thickness, but also the ability to remove solvent. This is because residual solvent on the drug eluting stent may induce adverse biological responses, compromise coating properties, induce drug degradation, and alter release profile. The ratio polymer-to-drug applied during each spray cycle can be 1:1, 2:1, 3:1, 4:1 or 5:1.

Thus, it was found that a release rate can be better controlled by applying many coats of a low percentage solution, e.g., 5% of the final coating weight, with a drying step between each spray cycle. Thus, in this example 20 coats are needed to produce the target coating weight. In order to make this coating process more feasible as a production-level method, while maintaining control over the solvent and solvent-drug-polymer interaction, as just discussed, an efficient in-process drying step was needed.

Dryers

Initial experiments configured a process to include a drying step using a commercially available air heater having a tubular conduit leading to a flared, or divergent opening. For example, the air heaters with flared openings offered by Osram Sylvania™, 131 Portsmouth Ave, Exeter N.H. 03833. These types of heaters are typically of metal construction and direct a gas stream down the tube and into the flared opening, which is inline with the tube. There is a flow-accelerating and re-shaping portion provided by the flared opening. The mean flow direction does not change as gas travels through the heater.

A flow profile for the gas, i.e., a gas exit velocity from the nozzle and gas temperature, was selected to produce a rapid drying time. It was expected that with an appropriate average heat transfer from the gas to the stent surface using either nozzle, i.e., selecting a suitable drying gas velocity and temperature, an efficient in process drying stage could be incorporated into the coating process, thereby making feasible a process of applying many low weight coatings while maintaining control over the solvent's effects on the drug-polymer morphology. The resulting drug release profile resulting from the use of the diverging channel or cylindrical nozzle types for solvent removal, did not, however, exhibit the desired properties. It was hypothesized that more control over the heat transfer might be needed.

Surprisingly and unexpectedly, it was found that when the heat transfer capacity and profile in the gas at the nozzle exit was modified, that is, made more uniform, there was significant improvement in the ability to control or tailor a drug release profile to suit the end objective. It was concluded, therefore, that not only is an efficient in-process drying step needed to produce an improved drug release profile, but also a more uniform heat transfer from the gas to the coated surface between each of several applied coatings.

The power or resources expended to remove solvent using a dryer is also an important consideration. During a cycling period when a medical device, such as a stent, is being coated, it is desirable to maintain the flow conditions. However, this can waste resources as expensive gas, such as Nitrogen, is being expended in order to maintain a steady state condition for the gas. In order to reduce these costs a closed-loop control was devised, which monitors temperature of the gas source at different flow rates. When a dryer is not in use, the head or inlet flow rate is reduced, thereby reducing the mass flow rate (to conserve gas). An increase in temperature of the exiting gas results. A thermocouple placed at the entrance to the dryer, and pressure monitor may be input as control parameters to continuously adjust heating coils to maintain the same temperature at the input when flow rate is reduced. By maintaining the same operating temperature when the gas flow rate is reduced, or the dryer idle, the startup time required to reach steady state flow is reduced. This provides significant cost savings in both material and power draw.

The efficiency of a dryer to remove solvent; that is, the amount of gas or energy needed per volume or weight of solvent removed was also considered. In a preferred embodiment, Nitrogen gas is used for the drying gas. In an effort to conserve resources, reduce process cycles and improve the uniformity or consistency of evaporation rates per unit area over a stent surface the flow properties around the stent were analyzed. Initially, it was believed that by placing a stent on a mandrel, rotating at a relatively high rate, and near the exit nozzle of the dryer all surfaces of the stent would be enveloped continuously within the hot gas and evaporated solvent would be quickly removed. However, it was discovered that the pressure differential between the gas stream exiting the nozzle at a relatively high rate of speed and surrounding ambient air was high enough to cause significant heat loss and interruption with the flow around the stent. It was found that if the pressure of the hot gas were increased in the vicinity of the stent, there was less interference as regards both the heat loss and uniformity of the heat transfer of the hot gas.

Two embodiments of structure designed to increase the efficiency and maintain uniformity of the gas properties surrounding the stent were developed. The first is a reflector placed behind the stent. the reflector is positioned so that as gas passes over the stent surface, it collects and maintained within the vicinity of the stent. The resulting pressure increase behind the stent has a tendency to reduce the amount of heat loss caused by the cooler ambient air in the vicinity of the stent.

The second embodiment is a gas expander or skirt positioned over the exit nozzle of the dryer. The gas expander may be a parabolic or conical type structure that functions to insulate the low-pressure gas exiting the nozzle from the cooler ambient air. As the gas passes through the expanding chamber, the gas is segregated from the ambient air. Its pressure may also increase. In a preferred embodiment, the gas expander is intended for segregating the hot gas from the surrounding cooler air. However, it will be appreciated that there are other advantages in using a gas expander according to the invention.

In view of the foregoing, the invention provides one or more of the following additional improvements over the art.

According to another aspect of invention, a method for coating a stent includes: (a) spraying the stent with a solution comprising 7% coating by weight and _93% solvent by weight, (b) removing solvent from the coated stent using a dryer such that following the removing solvent step only about 8% of the coating by weight is solvent remains in the coating, and repeating steps (a) and (b) until 100% of a desired coating weight is reached. Additional steps may include removing solvent from the stent between each, or after more than one coating of the solution is applied by directing a forced mass of gas towards the stent, the gas having a uniform velocity and temperature profile over the length of the stent wherein substantially only about 8% of the coating weight remains after applying the mass of forced gas.

Another aspect of the invention is a method for producing a desired release profile that includes a forced gas drying stage for uniformly removing solvent. In a preferred embodiment, solvent is uniformly removed for stents having lengths of 20 mm, 100 mm, 150 mm and 200 mm.

Another aspect of the invention is a dryer having an inlet conduit supplying an incoming gas stream and an exit area that produces a drying gas. The dryer includes a first gas conditioning chamber and a second gas conditioning chamber together forming a closed space for the conditioning of a gas supplied by a gas source and discharged at a nozzle exit, the gas having a mass flow rate that is the same at the nozzle exit as the mass flow rate supplied by the gas source during a steady state flow condition; the first gas conditioning chamber including a circular inlet coupled to the gas source and a linear array of apertures downstream of the circular inlet; and the second gas conditioning chamber including the linear array of apertures and an array of nozzle exit channels downstream of the linear array of apertures; wherein the dryer is adapted for producing a substantially uniform drying air mass from the linear array of nozzle exit channels.

The nozzle exit channels may be configured such that gas passing through the channels and exiting from the nozzle is noise reduced by forming vanes at the entrance to the channels, which may reduce the amplitude or frequency of fluid oscillations at the nozzle exit.

The dryer may further include a gas expander disposed about the linear array of nozzle exit nozzle channels. The gas expander may be formed by a parabolic or conical skirt that diverges outwardly from the nozzle exit such that gas pressure may decrease as it travels through the parabolic or conical skirt. The dryer may further include, or alternatively have a gas reflector disposed opposite the linear array of nozzle exit channels.

Another aspect of the invention relates to producing a coating weight by applying a light layer, drying the layer and then repeating these steps several times until a total coating weight is achieved. The number of layers can be greater than 19, greater than 30, greater than 40, and between 20 and 50 layers. A intermittent or in-process drying step can be included between each applied layer. The application of layers can be predetermined or determined by weighing the sprayed medical device and then continually applying layers until a desired weight is measured.

Another aspect of the invention relates to a heat nozzle for use during an in-process drying step for coating a drug eluting stent. This heat nozzle may provide a gas curtain with uniform velocity and temperature distribution, which improves the uniformity of solvent drying and reduces variability in drug release from the coating.

According to another aspect of invention a closed-loop controller is used to maintain a steady state flow temperature for variable gas flow rates. Using this controller, a dryer gas flow rate may be switched between an idle flow rate when the dryer is not being used and operational flow rate during a drying stage. As discussed earlier, it is essential that a rate or amount of solvent removal between coats can be predicted with some degree of certainty. By maintaining an essentially steady state flow whenever the stent is being dried, i.e., avoiding transient flow states, it becomes easier to predict the amount or rate of solvent removal. Moreover, by being able to reduce flow rates during periods of non-use, while maintaining a constant gas temperature, gas resources are conserved.

According to another aspect of the invention a method of drying a recently coated stent includes the steps of rotating the stent above a nozzle exit portion of a dryer to cause a gas produced by the dryer to effect a removal rate of solvent from the stent. The gas being produced by the steps of: supplying a gas to the dryer, the gas being delivered through a circular conduit such that the gas has an input mean flow direction into the dryer, decelerating the gas as it encounters a first chamber of the dryer, the first chamber presenting the gas with a first enlarged space arranged such that the gas is expanded in a direction perpendicular to the input mean flow direction, after the gas has been expanded in a direction perpendicular to the input mean flow direction, accelerating the expanded gas by forcing the gas through a linear array of apertures arranged in the direction perpendicular to the mean flow direction, the gas entering a second chamber, and decelerating, and then accelerating the gas as it fills the second chamber, the second chamber presenting the gas with a second enlarged space, followed by a narrowed space downstream of the second enlarged space and the nozzle exit downstream of the narrowed space. According to this method, the gas produces a uniform heat transfer from the gas to the stent over the entire surface of the rotating stent. For example, a uniform flow rate of 100 liters/min gas between the ranges of 100 and 120 degrees Celsius drying gas may be produced.

According to another aspect of the invention an apparatus for coating a stent includes a sprayer for applying a coating to a surface of the stent; and a dryer configured to remove a controlled percentage of solvent from a surface of the stent using a stream of gas supplied by the gas supply. The dryer is an in-process dryer that dries between coats.

The dryer may include a first gas conditioning chamber and a second gas conditioning chamber together forming a sealed space for the conditioning of a gas received from a gas source and discharged at a nozzle head, the mass flow rate supplied by the gas source being the same as the mass flow rate at the nozzle head during a steady state flow condition, the first gas conditioning chamber including a circular inlet coupled to the gas source and a linear array of apertures located downstream of the circular inlet, and the second gas conditioning chamber including the linear array of apertures and a line of nozzle exit channels downstream of the linear array of apertures; wherein the first gas conditioning chamber and the second gas conditioning chamber cooperate to convert gas received at the circular inlet to a gas stream having uniform velocity and temperature at the nozzle exit.

The apparatus may further include a control system for controlling the rate at which gas is supplied to the dryer and temperature of the gas exiting the dryer such that the gas temperature is maintained at a constant temperature for variable gas flow rates.

According to another aspect of invention, a method for coating a stent being movable between a sprayer and a dryer includes the steps of producing a steady state first mass flow rate of a drying gas from a nozzle exit of the dryer including the steps of opening a valve and adjusting a heater for heating the gas in response to a sensed change in the gas temperature; spraying a drug-polymer-solvent on a surface of the stent while the first mass flow rate steady state condition exists at the nozzle exit; before, or shortly after completing the application of a first coat of the drug-polymer-solvent on the stent, increasing the mass flow rate to the dryer while maintaining the same temperature including the step of adjusting the heater in response to a sensed change in the gas temperature, the dryer producing a stead state second mass flow rate; moving the stent to the dryer, or the dryer to the stent, and drying the stent using the gas exiting the dryer at the steady state second mass flow rate, wherein the second mass flow rate is characterized by a uniform, linear heat transfer from the gas to the stent surface such that a correspondingly uniform rate of solvent removal occurs on the stent surface, and the steady state temperature of the gas for the first mass flow rate is substantially the same as the steady state temperature of the gas for the second mass flow rate.

In accordance with another aspect of the invention a dryer may have a ratio of the total flux area for the array apertures to the nozzle exit channels of about 4:1; or the ratio of the total flux area for the array apertures to the inlet may be about 1.75:1 or 2:1; or the ratio of the total flux area for the nozzle exit channels to the inlet flux area is about 1:2.

In accordance with another aspect of invention, an array of nozzle exit channels have a length L, the depth of the combined chambers between inlet and exit is D, the height of the combined chambers between inlet and exit is H and the size of the diameter at the inlet is 2R, wherein the ratio of L to D, to H to 2R (L:D:H:2R) is about 1:(1/10):(1/3):(1/8); the ratio of L:2R is about 1:8; the ratio of L:D is about 1:1/10; or the ratio of L:H is about 1:1/3; and wherein the dryer is capable of producing a uniform temperature and velocity suitable for drying a stent for a flow rate of about 100 liters/min at a temperature in the range of 100 to 120 degrees Celsius.

In accordance with another aspect of invention a dryer exit nozzle length is sized to minimize variations at the edges of the stent. The length of the array of nozzle channels may have a length that is about 125% of the length of a stent, or 1.5 times the length of a stent length for which the dryer is configured for drying to produce a uniform heat transfer from the gas to the stent surface.

In accordance with another aspect of invention, a gas expander is configured for maintaining a uniform heat transfer near the stent surface, the stent having a diameter D, wherein the height of the expander is about four times D, the mouth of the diameter is between two times and four times D, and the stent is placed about a D distance from the mouth. A gas expander having a height to mouth ratio of 1:1 in some embodiments. In some embodiments, a stent and drying apparatus having a mechanism for moving a stent between dryer and sprayer may be configured for placing a stent about one stent diameter within the gas expander, or in other embodiments, about a distance of 25% of the height of the gas expander from the mouth of the expander. The stent may be placed closer to the nozzle exit. In tests conducted using recently coated stents it was found that an optimal distance was about this 25% (preferably a diameter distance for a 4D×4D gas expander) from the nozzle mouth, which distance provided the optimal condition, based on two variables—stability of stent and efficiency in drying. Thus, according to the embodiments an optimal distance, or range is discovered. The optimal position of the stent may be found through an optimization subject to a constraint of three variables: (1) the type of stent support, (2) type of gas expander and nature of the (3) heat transfer from gas to stent. Parameter (2) is discussed earlier.

Parameter (1) relates to the support used for the stent and, in particular, the amount of motion allowed when the stent is impacted by fast moving air. In a preferred embodiment, the stent is preferably supported on a mandrel that provides a loose fit, indeed pseudo unstable, to minimize coating defects at surfaces of the stent making contact with the mandrel. Examples of mandrels that provide this loose fit are provided in U.S. Pat. No. 7,572,336 and U.S. application Ser. No. 12/554,671. These designs cause the contact points to constantly change as the stent is rotated, thereby minimizing coating defects. As such, the stent is loosely held on the mandrel and therefore more sensitive to high momentum, oscillating, periodic or random gas jostling of the stent. If the stent was instead held firmly, then the stent may be placed closely to the nozzle and solvent removed more rapidly (hence gas drying efficiency goes up). However, one then begins to develop unacceptable coating defects in the form of bridges, etc. between the stent and mandrel surfaces. Thus, the optimal distance is found by constraining at least two variables—the size of the gas expander and degree to which the stent mandrel and stent can sustain random or periodic loading caused by the exiting gas. Parameter (3) relates to the heat transfer environment. In one embodiment nitrogen gas exiting at a rate of 100 liters/min and within the range of 100 to 120 degrees Celsius is chosen in combination with the mandrel described in U.S. application Ser. No. 12/554,671 filed Sep. 4, 2009 (e.g., apparatus shown in FIG. 4 or 7 and description referencing these drawings which will be referred to herein as a loose-fitting or instantaneous contact-type mandrel support, mandrel support that intentionally causes wobbling or relative movement between stent and mandrel when the mandrel is rotated), and the expander dimensions depicted in FIG. 6 to produce a distance of one diameter within the mouth. In other embodiments the stent may be at least one diameter within the mouth, or 25% of the expander height from the mouth. Additionally, the gas expander sides are formed of heat-insulting PEEK material.

According to another aspect of invention, a method of drying a stent, comprising the steps of dryer having an inlet conduit supplying an incoming gas stream and an exit area that produces a drying gas, comprises placing the stent near an array of nozzle exit channels; and placing the stent within a gas expander such that the stent is between a mouth of the expander and the array of nozzle exit channels; wherein the dryer is adapted for producing a substantially uniform drying air mass from the linear array of nozzle exit channels. In one particular embodiment, the stent is placed at an optimal distance from the nozzle exit channel, the optimal distance being selected according to the constraints of the selected dimensions of the gas expander for the stent, the heat transfer properties of the gas including heat loss rate for exiting gas, and the minimum distance from the nozzle exit to avoid unacceptable jostling or motion of the stent when the stent is being supported by loose-fitting mandrel support, or the stent wobbles when rotated by the mandrel. In one embodiment the distance is one stent diameter within the mouth for a gas expander with dimensions of 4D×4D and made of PEEK material, the flow rate is 100 liters/min between 100-120 degrees C., and the mandrel supports the stent at non-constant contact points as the stent rotates, i.e., a wobbling stent-type mandrel.

Spray Nozzles

With the goal of obtaining a more consistent and predictable drug-release profile over the length of the stent, and obtain improved efficiency and less wasted resources, the ability of a spray nozzle to deposit a consistent pattern of drug-polymer-solvent was also considered. Another aspect of invention concerns the uniformity or consistency of the spray pattern during the spraying step in accordance with the foregoing need. According to this aspect of invention, there is a method of making a spray nozzle, comprising: forming a housing from a first metal having a first hardness, the housing including a first bore for the passage of an atomizing gas and a second bore for receiving cannulae, the second bore having a first and second diameter, the first diameter forming at its upper end a ledge; forming a cannulae from of a second metal, the second metal having a second hardness, less than the first hardness, the cannulae including a tapered bore for receiving fluid, such that the tapered bore reduces a pressure drop for fluid disposed within the tapered bore a stepped outer diameter, and a polished lower end; forming a polished nozzle cap that is devoid of scratches or abrasions on its inner and outer surface near a nozzle orifice; press-fitting the cannulae into the second bore such that the stepped outer diameter is placed against the ledge of the housing bore; and fitting the nozzle at a nozzle exit so that the orifice is aligned with an exit aperture of the cannulae.

According to another aspect of invention a method for coating a stent with a drug-polymer solution, comprises spraying the stent using a spray nozzle, including the steps of delivering a first metered supply of an atomizing gas through a first bore in fluid communication with a nozzle orifice, and a drug-polymer solvent fluid through a second bore in fluid communication with the nozzle orifice; after spraying the stent, moving the stent to a dryer for drying the stent; and while the stent is being dried, applying a second metered supply of a gas to the nozzle, the second metered supply being different from the first metered supply, wherein the second metered supply is adapted to reduce instances of clogging or buildup of drug-polymer solvent proximal the nozzle orifice when the stent is being dried. The step of while the stent is being dried, applying a second metered supply of a gas to the nozzle, the second metered supply being different from the first metered supply, may further include disposing a second source of pressured gas, external the nozzle, adjacent the nozzle and directed towards the nozzle, and applying the second metered supply of gas to the nozzle while a third metered supply of gas is applied to the nozzle by way of the second source of pressurized gas. The step of disposing a second source of pressured gas, external the nozzle, adjacent the nozzle and directed towards the nozzle may further include disposing a second nozzle having a orifice orientated to direct a stream of gas towards the orifice of the nozzle at an angle of between 20-40 degrees relative to a lower face of the nozzle. The coating applied to the stent may be a solution of about 93% solvent and about 7% drug-polymer solution. The solvent may be DMAc.

INCORPORATION BY REFERENCE

All publications and patent applications mentioned in this specification are herein incorporated by reference to the same extent as if each individual publication or patent application was specifically and individually indicated to be incorporated by reference, and as if each said individual publication or patent application was fully set forth, including any figures, herein.

DETAILED DESCRIPTION OF EMBODIMENTS

According to a preferred implementation of the invention, a sprayer and heat nozzle is used to form a drug-eluting coat on a surface of a stent. A stent is an intravascular prosthesis that is delivered and implanted within a patient's vasculature or other bodily cavities and lumens by a balloon catheter for balloon expandable stents and by a catheter with an outer stent restraining sheath for self expanding stents. The structure of a stent is typically composed of scaffolding, substrate, or base material that includes a pattern or network of interconnecting structural elements often referred to in the art as struts or bar arms. A stent typically has a plurality of cylindrical elements having a radial stiffness and struts connecting the cylindrical elements. Lengthwise the stent is supported mostly by only the flexural rigidity of slender-beam-like linking elements, which give the stent longitudinal flexibility. Examples of the structure and surface topology of medical devices such as a stent and catheter are disclosed by U.S. Pat. Nos. 4,733,665, 4,800,882, 4,886,062, 5,514,154, 5,569,295, and 5,507,768.

As discussed earlier, one aspect of the stent coating process that has been simplified, or improved, as a result of the dryer according to the disclosure, is the ability to predict more consistently the rate of solvent removal and variation over the length of the stent of that rate. Increasing the predictability of a solvent's presence in the applied coating, or remaining when determining a final weight can greatly increase the ability and/or efficiency in which a predictable release rate for a drug can be provided in a medical device, in the form of an applied coating.

Moreover, as the design or desired loading of polymer-drug on the stent is determined from the measured weight, it will be readily appreciated that there needs to be an accurate, reliable and repeatable process for being able to determine the amount and distribution of solvent remaining over the length of the stent. This is especially true when less volatile solvents are used, e.g., DMAc as opposed to the more volatile solvent Acetone. Since it is expected that a greater percentage of solvent will remain after drying for solvents having higher boiling points, the coating is more susceptible to variations in a solvent's presence over the stent surface and/or across the coating thickness.

The disclosure provides examples of spraying/drying components suited for addressing the previously discussed drawbacks and limitations in the art pertaining to a drug-eluting coating applied via a drug-polymer dissolved in a solvent.

Dryer Assembly

Figure 1:
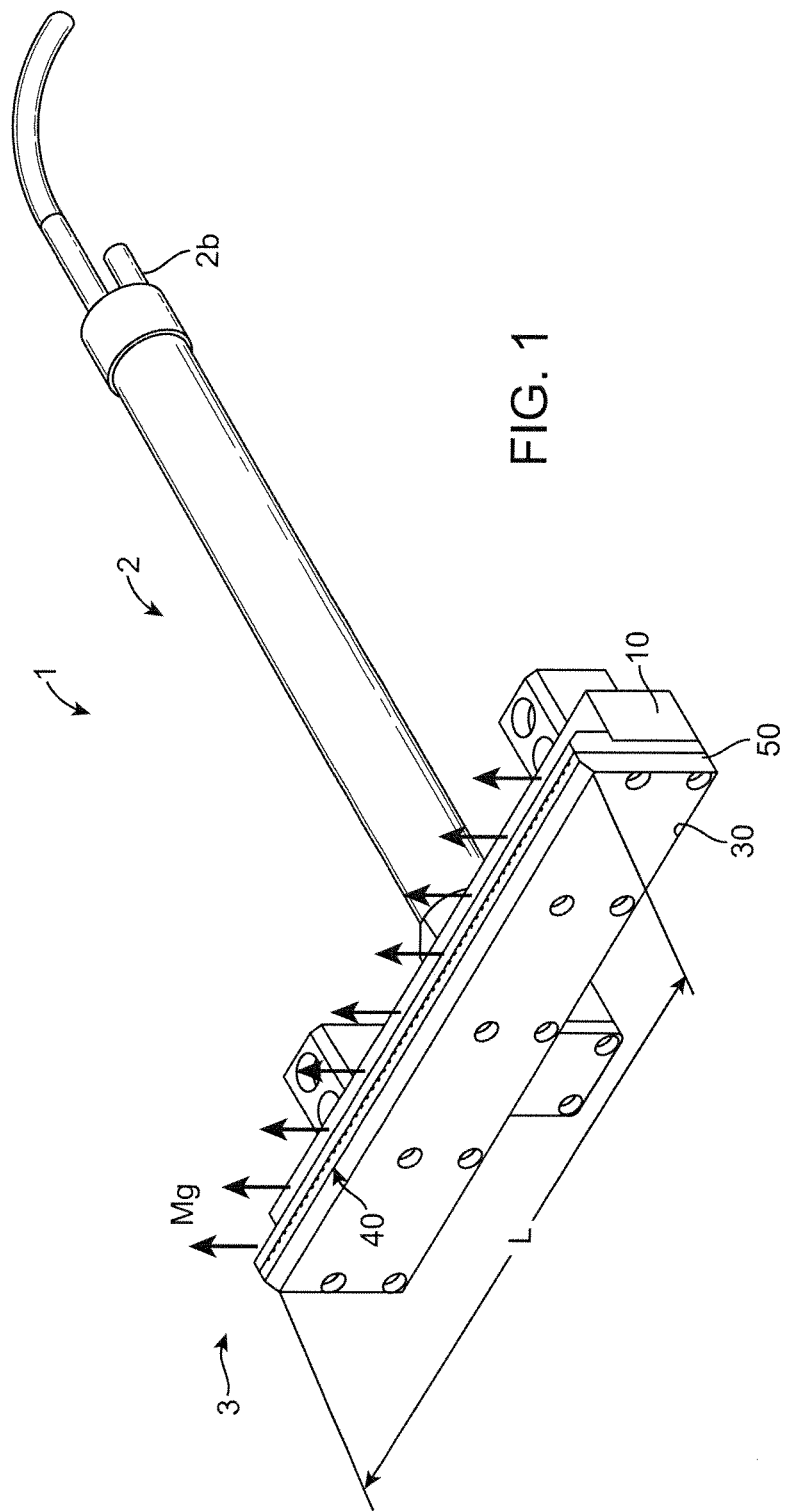
FIG. 1 is a perspective view of a dryer according to one aspect of the disclosure. The dryer is supplied a gas through a conduit of a heater assembly.

FIG. 1 shows a perspective view of a dryer 1 according to one aspect of the disclosure. The dryer 1 may be included as a component used in a stent coating process. Such a stent coating station implementing a process may include a sprayer, the dryer 1 and actuators for selectively placing the sprayer and dryer over the stent between spraying and drying steps, respectively. Examples of a stent coating system that may adopt principles of the disclosure are described in U.S. patent application Ser. Nos. 12/497,133; 12/027,947 and 11/764,006. In these examples, the dryer(s) and spray nozzle(s) described therein may use a dryer and spray nozzle according to the disclosure, as will be understood.

A coating process may be preprogrammed, or programmed on the fly to adjust parameters such as number of coats, or passes with the sprayer between drying steps, number of cycles of spraying and drying, etc. These and related parameters may be governed by the polymer-drug or solvent used, type of stent or medical device being coated, e.g., surface geometry. In particular embodiments the protocol for coating a stent may be governed by a predetermined number of coating cycles, i.e., spraying then drying, based on an analytically determined final coating weight, or by intermittent weighing of the stent to determine the number of cycles needed to arrive at the target coating weight.

The stent may be held in a mandrel and rotated as the sprayer applies a drug-polymer dissolved in a solvent, e.g., DMAc, to the surface of the stent. After one, two or more passes over the body of the stent with the sprayer, the dryer 1 is moved into position over the stent. The nozzle exit 3 is placed beneath the stent (or the stent moved into a drying position above the nozzle exit 3) at this stage of the process, so that the stent length extends lengthwise over the nozzle 3, i.e., parallel to the direction measuring the length L in FIG. 1. Once in position, a mass of heated gas exits from the nozzle exit 3 to accelerate the evaporation, or boiling-off of solvent from the coated stent surface. In a preferred embodiment, this sprayer-dryer coating process is repeated until a final coating weight of drug-polymer and remaining solvent is measured. During each drying stage of preferred embodiments, the gas produces a uniform heat transfer across the surface of 100 mm, 150 mm, and 200 mm stent. After a final coating weight has been reached, the stent may be placed in an oven for an extended period to remove additional solvent.

Figure 2A:
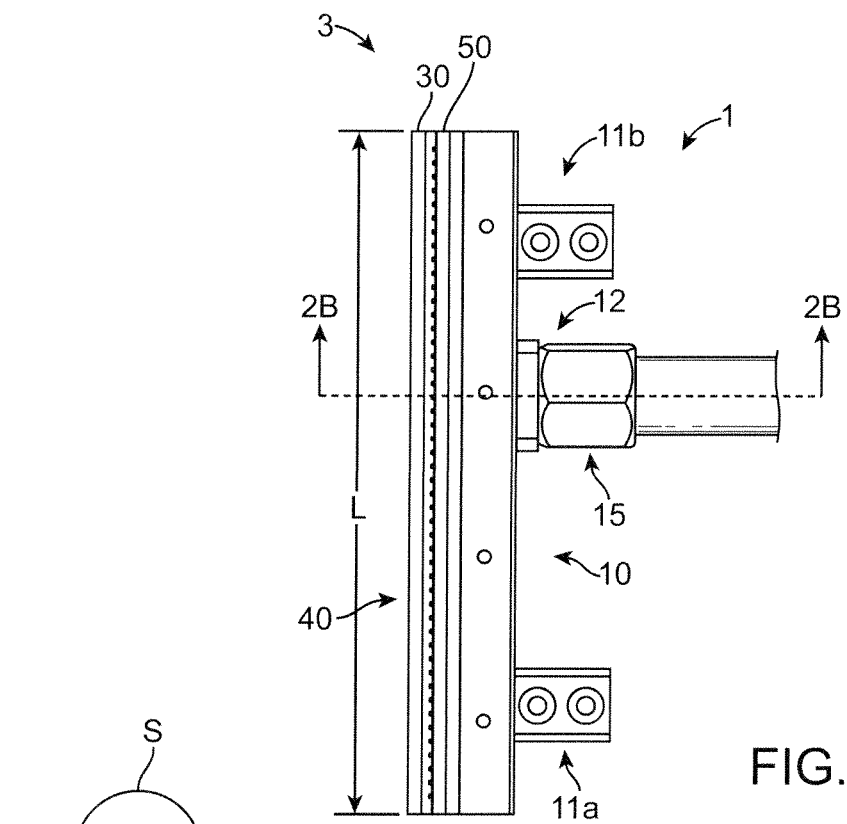
FIG. 2A is a top view of the dryer of FIG. 1.
Figure 2B:
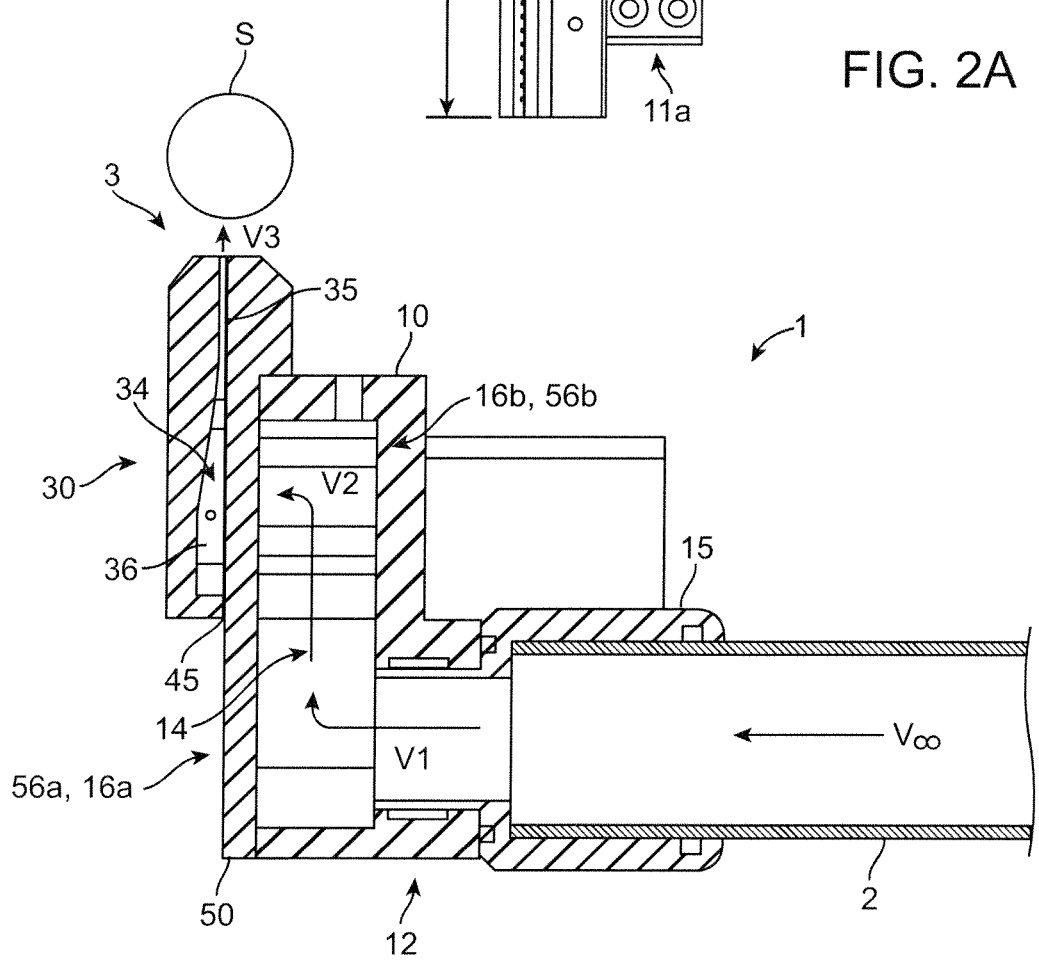
FIG. 2B is a side cross-sectional view of the dryer of FIG. 1 taken at section AB-2B in FIG. 2A. As depicted here, a gas stream $v_\infty$ enters the dryer at an entrance. The gas velocity is abruptly decreased ($v_1$) as it encounters a wall, at which point it is forced upwardly. The increased pressure causes the gas to expand into an upper chamber of a plenum ($v_2$). Here the high pressure area causes the gas to make another right hand turn and exit at higher velocity through a diffuser. The gas in (V1) enters a second chamber. This chamber slows the gas down again, then causes it to accelerate upwardly until it exits from a nozzle exit ($v_3$). The gas exiting the nozzle is uniform in temperature and velocity and extends over a linear length (gas curtain) for drying a stent (s) disposed over the nozzle.

As illustrated, the dryer's exit nozzle 3 is configured to produce the mass of heated gas (represented by the array of vectors $M_g$ extending upward from the nozzle exit 3 in FIG. 1) over a linear length L, which may correspond to the length of the coated stent positioned for drying. FIG. 2B, which is a partial side cross-sectional view of dryer 1 taken at section 2B-2B in FIG. 2A, shows the stent S in position opposite the nozzle exit 3. The drying gas, e.g., heated nitrogen, is supplied through a gas supply 2b connected to a heater assembly 2. The heater assembly 2 includes a tubular conduit with heating coils (not shown) exposed to the gas stream as it travels towards the plenum 10 (as represented by vector $V_\infty$ in FIG. 2B). The coils are connected to a power source via a power connection 2a.

The gas traveling over the length of the heater assembly 2 is heated to a desired temperature and the gas pressure is known. Thus, gas entering the plenum 10 has a predetermined velocity and temperature (a thermocouple may be placed near the entrance to measure gas temperature). The gas may be treated as an incompressible fluid between the entrance 12 of the dryer 1 and exit 3. The velocity of gas passing through any cross-section, therefore, may be considered inversely proportional to the size of the cross-section assuming no significant heat loss through the walls of the dryer (conservation of mass). In a preferred embodiment, the plenum, diffuser and nozzle portions of the dryer are made of PEEK plastic to minimize heat flow between the interior of the dryer and exterior environment. PEEK may be used for maximum temperatures of up to 200 degrees Celsius.

Figure 3A:
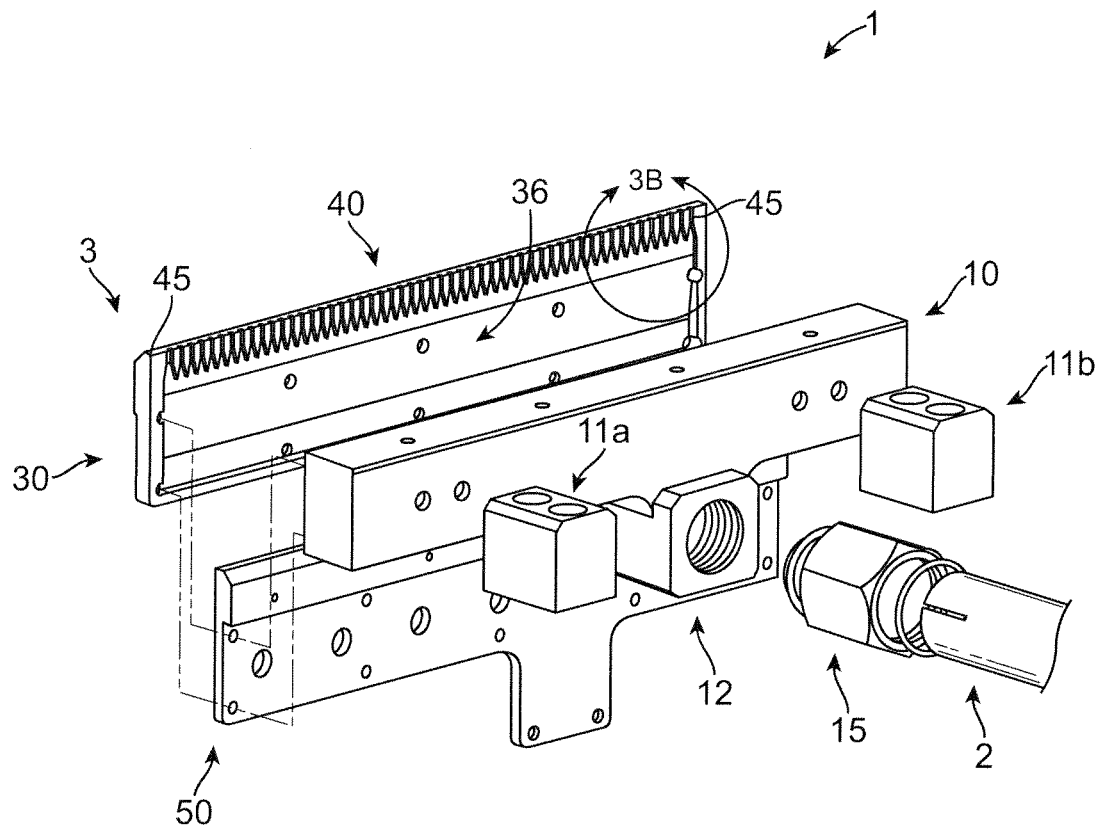
FIG. 3A is a forwardly looking, exploded assembly view in perspective showing component parts of the dryer of FIG. 1.
Figure 4:
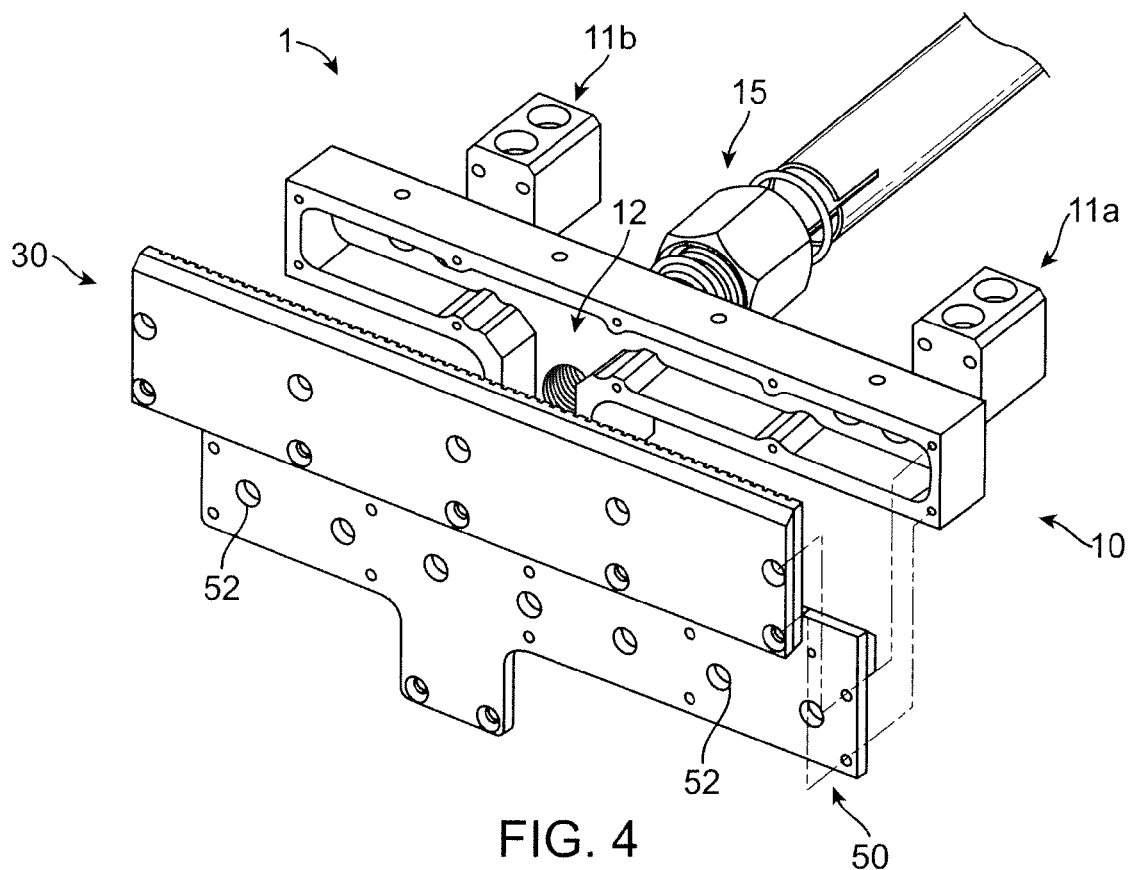
FIG. 4 is a rearwardly looking, exploded assembly view in perspective showing component parts of the dryer of FIG. 1.

FIG. 4 is a rearwardly-looking exploded view of the dryer 1 showing its component parts, i.e., a plenum 10, a diffuser plate 50 and a nozzle 30. FIG. 3A is a forwardly-looking exploded view of the dryer 1 showing these same components. Mounting blocks 11a, 11b are used to mount the dryer 1 to a support of a sprayer-dryer assembly, e.g., the spray-dryer assembly 350 of FIG. 7B, and a coupling or threaded sleeve 15 connects the heater assembly 2 to the dryer 1 entrance 12.

The diffuser 50, disposed, between the plenum 10 and nozzle 30, acts a divider between two distinct and functionally different chambers for conditioning the incoming gas. These are the plenum volume, space or chamber 14 and nozzle volume, space, or chamber 34 for flow conditioning. The assembly of the components may be described as the plenum 10 and diffuser 50 portions together forming a plenum chamber 14 and the nozzle 30 and diffuser 50 portions together forming a nozzle chamber 34 for dryer 1. The diffuser 50 includes apertures 52 that may be of the same diameter and evenly spaced over the length (seven are shown in FIG. 4) for passage of gas from the plenum chamber 14 to the nozzle chamber 34 after the gas has been first conditioned (as describe below) by the plenum chamber 14. The gas mass $M_g$ is then conditioned for a second time in the nozzle chamber 34 before it exits the nozzle exit 3 from the nozzle chamber 34.

Plenum chamber 14 features are described with reference to FIGS. 2B, 4, 4A and 4B. The plenum chamber 14 is generally T-shaped, formed by a cavity 16 of the plenum 10 and the rear face 56 of the diffuser plate 50. This chamber is sealed, with the exception of the upstream cylindrical entrance passage 12 (incoming gas from heater assembly 12) and the downstream array of apertures 52 that provide a fluid passage between the plenum chamber 14 and the nozzle chamber 34.

Figure 4A:
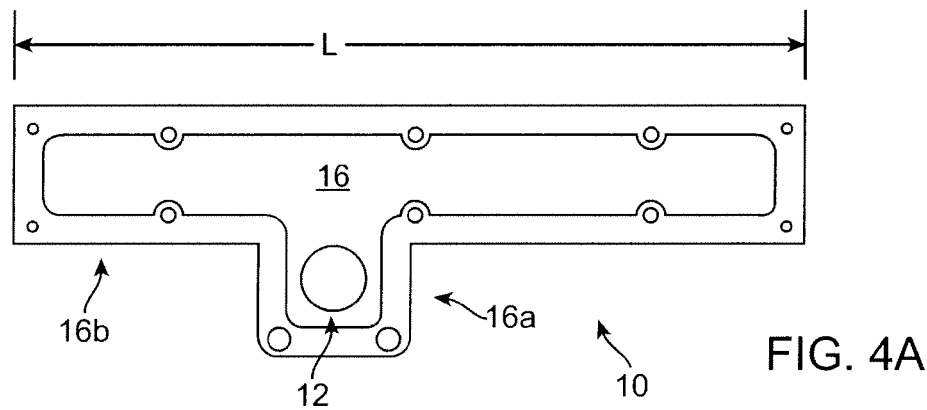
FIG. 4A is a front view of a plenum portion of the dryer of FIG. 1
Figure 4B:
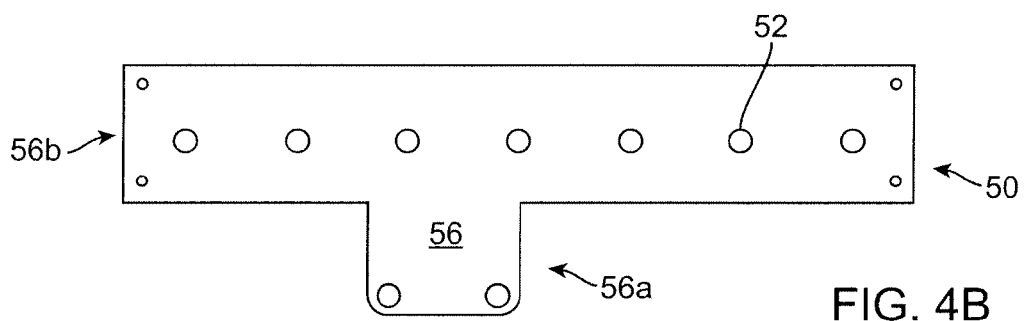
FIG. 4B is a frontal view of portion of the dryer of FIG. 1. The diffuser is mated with the plenum to form a T-shaped gas conditioning chamber. Flow apertures are formed on the diffuser.
Figure 5:
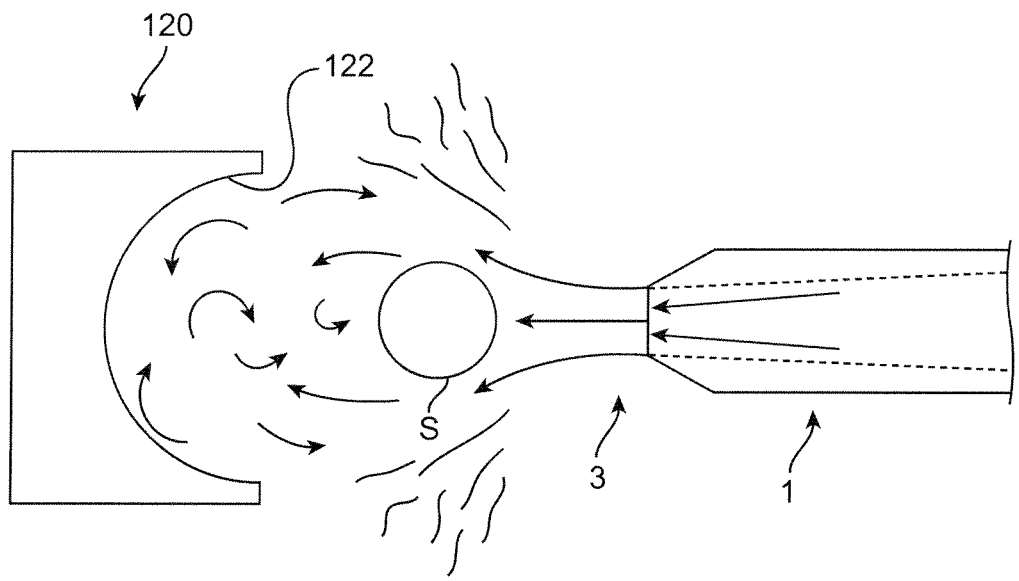
FIG. 5 is a schematic view of a dryer and reflector drying the stent S. Illustrated in this schematic are streamlines of heated gas exiting the nozzle of the dryer of FIG. 1 and reflecting or being constrained to form an area of high pressure in the vicinity of the stent.

An upper portion 16b formed by the section extending from left to right in FIG. 4A and preferably having the length L (see also FIG. 1) mates with the diffuser plate 56 portion 56b having the array of apertures 52. A lower portion 16a formed by the section containing the entrance 12 mates with the diffuser portion 56a that is devoid of an aperture or opening to the nozzle 34 chamber. Thus, when gas enters the plenum chamber 14 lower portion from the cylindrical opening 12, it is immediately decelerated and gas pressure increases. This forces gas upwards into the expanded space of the plenum chamber 14. Gas accumulated under this pressure in the upper portion 16b then exits from the plenum chamber 14 and enters the nozzle chamber 34 via the array of apertures 52, which are arranged essentially over the same length L as the exit nozzle 3, but with a larger opening (or total flux area) than the exits 40 at the nozzle 3.

In one embodiment the total flux area for gas flow through the apertures is about 0.344 in$^2$, as compared to 0.0864 in$^2$ at the nozzle exit 3. The total flux area at the inlet is about 0.196 in$^2$. The ratio of the inlet to diffuser total flux area may be about 1:1.75, about 1:2 or between about 1.5:1 and 2:1. The ratio of the diffuser to the exit total flux area may be about 4:1. In one embodiment, the ratio of the exit total flux area (E) to the diffuser total flux area (D) to the inlet total flux area (I), i.e., the quantity E:D:I, is between about 1:4:2 to 1:4:2.5. In other embodiments, the diffuser total flux area is greater than the inlet total flux area and the inlet total flux area is greater than the nozzle exit channel total flux area.

Nozzle chamber 34 features are described with reference to FIGS. 2B, 3, 3A and 4. As can be best appreciated in FIGS. 3 and 3A, the chamber 34 is formed by mating the front face of the diffuser 50 with the nozzle 30 so that surfaces 35 and 45 of the nozzle 30 abut the face of the diffuser 50 (FIG. 2B). The diffuser 30 has formed therein a cavity 36 bounded by surfaces 35 and 45. At the upper end (near the nozzle exit 3) a linear array of nozzle exit channels 40 form rectangular notches 42 over the length L of the cavity 36. When the cavity 36 is mated with the flat, opposing face of the diffuser 50, the channels 40 provide an array of rectangular passageways that produce a flow pattern having reduced turbulence, and more uniform gas flow from the nozzle chamber 34 out through the nozzle exit 3 along the length L.

Referring to FIGS. 2B, 3 and 3A, at the lower end of the chamber 34 there is a relatively wide base portion, followed by a tapered portion. At the upper end of the tapered portion the chamber has its narrowest point, which is where lower, tapered ends 43 are formed to reduce turbulence and therefore noise at the nozzle exit 3 (as described in greater detail below). The chamber 34 is therefore configured as a converging channel extending upwards in FIG. 2B, and at a right angle to the average gas flow direction through the apertures 52. That is, the gas flow makes a 90 degree turn upwards when it reaches the nozzle chamber 34. Pressure builds in the lower portion of the chamber 34, as a result, then gradually reduces (as the section narrows) until the gas exits from the nozzle exit 3 where there is a sharp decrease in pressure to atmospheric pressure.

Figure 3B:
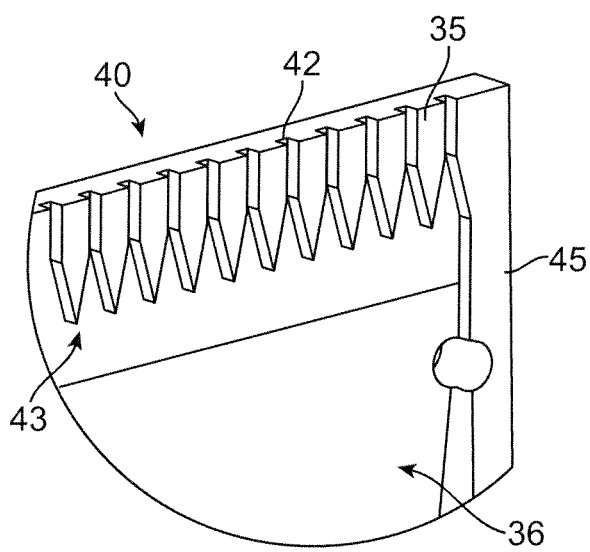
FIG. 3B is a close-up view of a portion of a nozzle component of the dryer near the nozzle exit taken from section 3B in FIG. 3A.

Referring to FIG. 3B, at the lower end of each of the channels 45 there are sloped surfaces that form a converging point. Placed side by side the channels 40 having the tapered end 43 form a converging channel for gas flow traveling up from the lower portion of the chamber 34. It was found that by forming the tapered ends 43, or converging channels leading to the exit 3, the flow tended to be more laminar at the exit. Additionally, vibrations presumably caused by oscillating gas flow emanating from the exits 40 was significantly reduced when the ends of channels 40 were tapered. As a result, there was a significant reduction in vibro-acoustic noise caused by the exiting gas mass $M_g$. This reduced the noise that operators of a spray station would encounter during operation.

In a preferred embodiment, the ratio of output length (L), i.e., length of array of channels openings 40 at exit 3, to the input diameter at the inlet 12 (D), to the height of the internal space from the plenum chamber 14 lower surface to exit 3 (H), to the depth from the leftmost wall of the nozzle chamber 34 in FIG. 2B to the rightmost wall of the plenum chamber 14 (2R), or the ratio L:D:H:2R is about 1: (1/10): (1/3): (1/8). Thus, for a length (L) of 100 mm, the depth of the gas conditioning chambers is about mm, the height of the gas conditioning chambers is about 33 mm and the diameter at the inlet is about 10 mm.

According to one embodiment of the dryer 1, which is configured for drying a stent having a length of 200 mm, the length of the nozzle exit is preferably about 250 mm to ensure that the ends of the stent are not subject to variations in the flow or influence by ambient air at the ends of the nozzle, so called end effects. As explained in detail above, these values were obtained from results indicating the lengths of the nozzle exit relative to the stent length that would not produce an inconsistent or irregular rate of removal of solvent near the edges. The verification of this minimal length was determined only through testing (if sensitive nature of remaining solvent's effect on release rate were not a concern, of course one would prefer having the nozzle gas exit being more closer to stent length to conserve gas resources and increase drying efficiency). In some embodiments the nozzle length may be about 25% wider than the longest stent length suited for the dryer, so that end effects are negligible. In other embodiments, the total length of the nozzle may be about 1.5 times the total length of the longest stent suitable for the dryer, so that end effects, i.e., effect on solvent irregularity and therefore release rate, are negligible.

According to a preferred embodiment, a dryer flow setting is 100 standard liters/minute gas flow, and a temperature setting of approximately 100 to 120 degrees C.

Closed-Loop Controller

A gas flow rate through the heater assembly 2 in FIG. 1 may be monitored/controlled by a commercially available mass flow regulator (not shown). For example, such a mass flow regulator may be used to operate an adjustable valve coupling the gas supply line 2b to a gas source to produce the desired flow rate. One example of a suitable mass flow regulator is the Aalborg GFCS series mass flow regulator. A use of a mass flow regulator and related control system suitable for use with aspects of the disclosure is described in U.S. application Ser. No. 12/540,302.

During a coating process, the dryer is not in use when the stent is being coated. If the dryer is shut down or the flow rate reduced the temperature of the gas at the entrance to the plenum 10 of the dryer 1 will decrease. If the stent is moved into position above the nozzle exit 3 for drying and the valve opened to increase the flow rate, there will be a period of transient flow. It is desirable to avoid a period of solvent removal by transient gas flow, since the rate or amount of solvent removal by transient flow can be difficult to predict. It is preferred, therefore, that the stent is dried only during steady state flow conditions.

If gas flow at the dryer is instead maintained at a constant rate, then the temperature may be maintained. However, this wastes gas resources. It would be desirable if the gas flow rate could be reduced when the dryer is not in use while holding the gas temperature at a constant value.

Figure 7A:
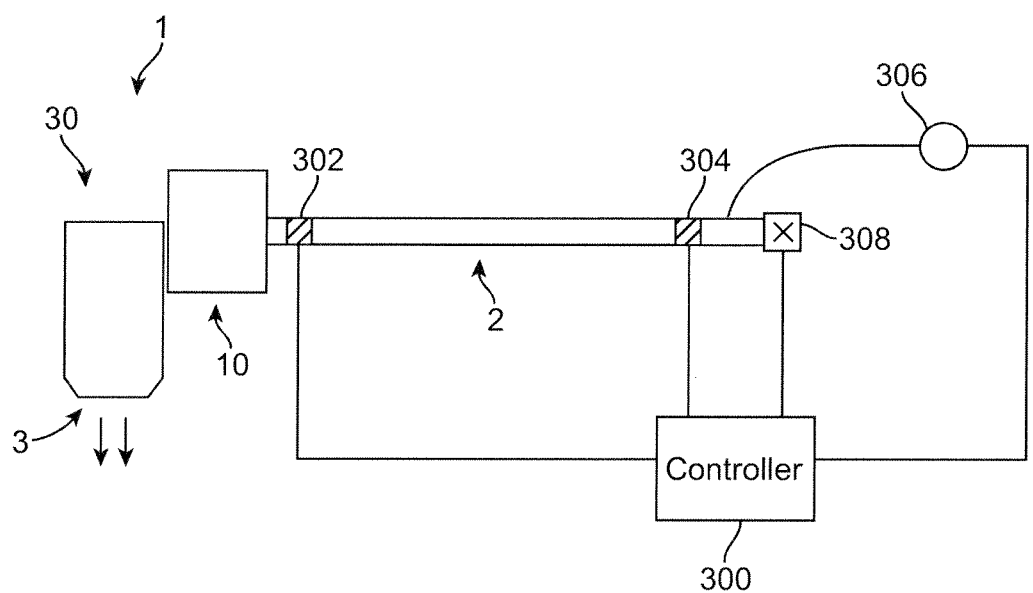
FIG. 7A is a schematic view of gas flow controller for the dryer of FIG. 1. The controller is configured for producing a constant temperature gas flow into the dryer for variable and steady state flow rates.
Figure 7B:
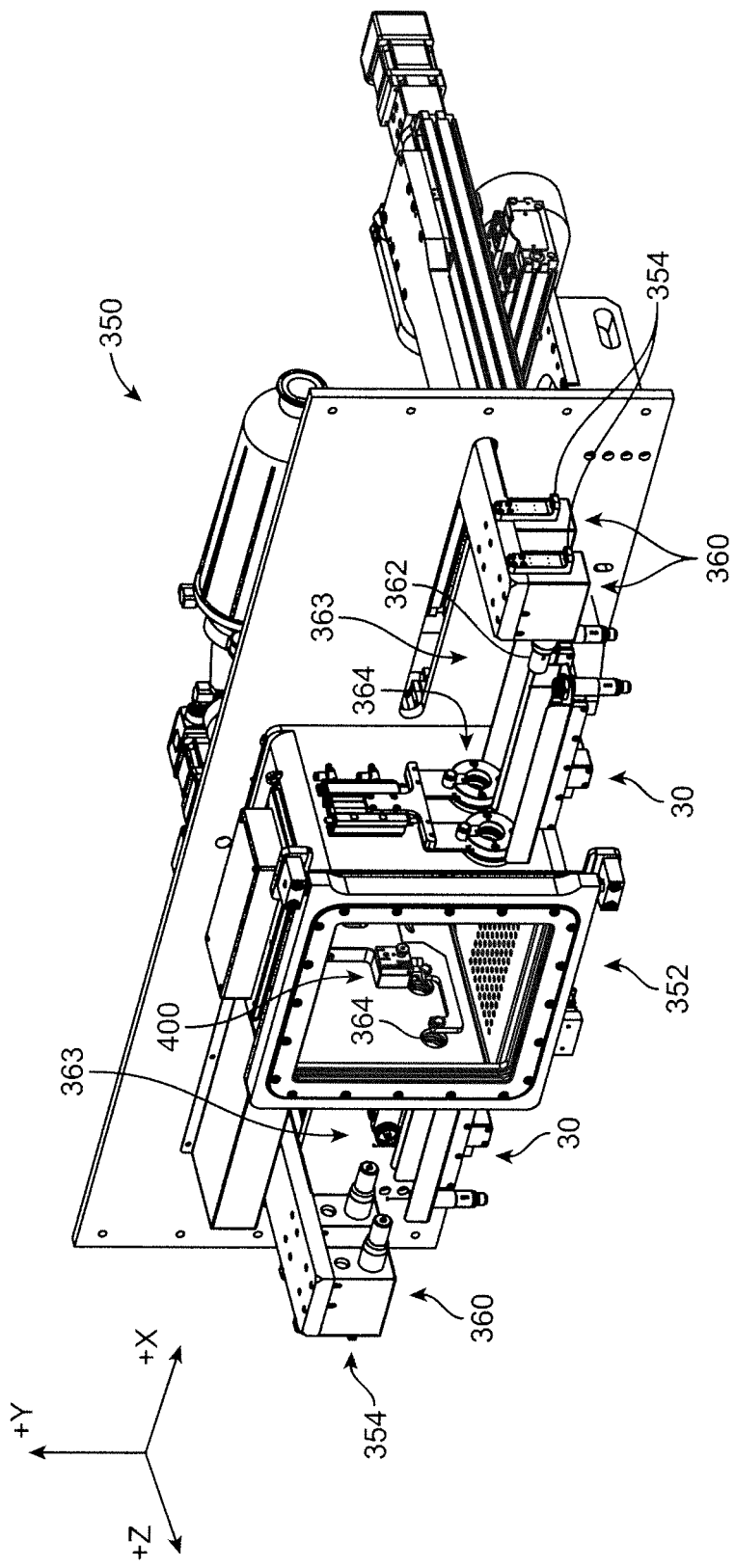
FIG. 7B is a perspective view of a stent spraying and drying assembly incorporating aspects of the disclosure.

To meet this need, a closed loop control is preferably implemented with a stent dryer system according to the disclosure, so that the gas temperature may be maintained at variable flow rates. Referring to FIG. 7A, a schematic of this closed-loop control is illustrated. A controller 300 continuously receives input temperatures at the entrance of the plenum from a thermocouple 302 and the gas flow rate upstream of the plenum entrance from a flow sensor 304. The controller 300 may be programmed to reduce the gas flow rate when the dryer is not in use, and increase the gas flow rate when the stent is ready to be moved into position above the nozzle exit 3.

Figure 6:
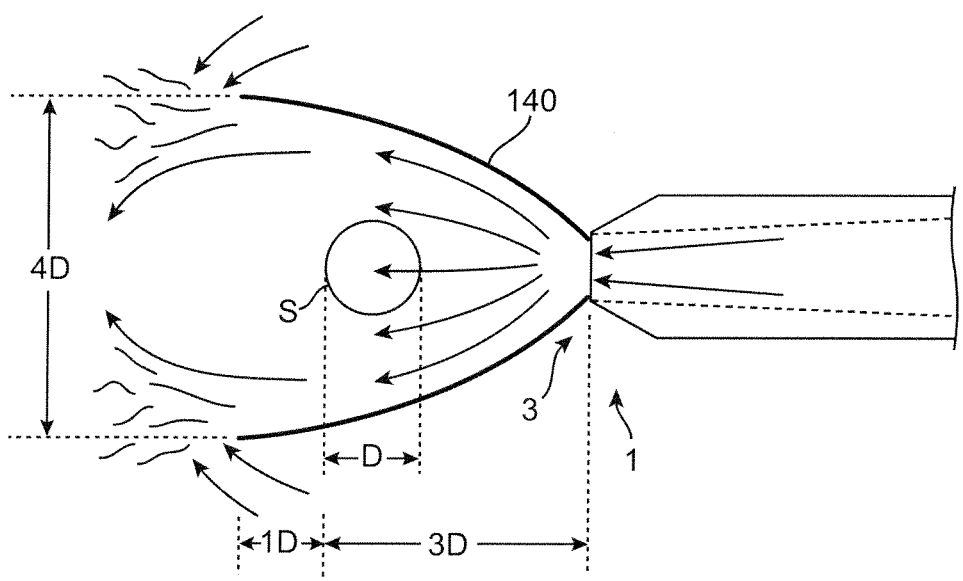
FIG. 6 is a schematic view of a dryer and gas expander drying the stent S. Illustrated in this schematic are streamlines of heated gas being expanded as the gas travels through the gas expander. The gas expander acts as a partition that segregates the hot gas as it expands from the surrounding cool gas and improves the uniformity of the gas properties in the vicinity of the stent.

As the flow rate is adjusted by opening/closing the adjustable valve 308, the controller senses a change in temperature from input received at the thermocouple 302, at which point it will increase/decrease the power delivered to the heating coils by affecting control 306 for power so that the temperature remains constant, regardless of the actual flow rate. Thus, according to this aspect of the disclosure, a dryer system may be operated at variable flow rates during a coating process while maintaining a substantially steady state gas flow during the drying stage, or a minimal period of transient flow conditions until a steady state condition is reached. This improves/maintains the predictability of solvent removal during drying, minimizes down time and allows gas resources to be conserved. The coated stent is almost immediately subject to the drying step and dried in a manner that allows the improved prediction of solvent removal. As discussed earlier, this is a critical step in the process of producing a predictable release rate for a drug-eluting stent and accurate assessment of whether the desired drug-polymer coating weight has been reached.

A closed loop controller in accordance with the foregoing may be incorporated into a spray-dryer assembly of the type described in U.S. application Ser. No. 12/540,302. FIG. 7B is a reproduction of FIG. 3A of this application. In this assembly 350, a pair of stents on mandrels (not shown) are supported from right-side spindle assemblies 360 (spindles 362), which are disposed on respective left and right sides of a spray isolator enclosure 352. According to this configuration, a pair of supported stents on one side of the spray isolator enclosure 352 are dried while a pair of stents supported on the opposite side of the spray chamber 352 are sprayed. The spindle assemblies 360 rotate the stents during drying and spraying. A spray nozzle 400 is shown disposed within the chamber. When moved into, or out of the spray isolator enclosure 352 the stents on mandrels are passed through openings 364. A left and right pair of dryer nozzles (each being the nozzle 30 of dryer 1) are shown disposed between the respective left-side and right-side spindle assemblies 360 in FIG. 7B and the spray isolator enclosure 352 (only one of these left and right pairs of nozzles 30, respectively, is visible in this view). The stents are dried in area 363.

One of a pair of left and right stents may be sprayed and dried using the controller 300 assembly 350 according to the following steps. First, the stents are placed within the spray isolator enclosure 352 for spraying. During, or prior to the spraying, the gas flow to the nozzles 30 is set at an idle setting with the controller increasing the power to the heating coils as necessary (based on input received from the thermocouple 302) until the temperature of the gas flow reaches a steady state condition. A transducer 354, mounted on a spindle assembly 360, may also be used to measure the exit temperature above the nozzle.

After, or just prior to completion of an application of coating material on the stents using the nozzle 400, the controller 300 increases the gas flow temperature to the drying gas flow rate. While the gas flow is being increased, the controller 300 monitors the temperature at the plenum entrance 12 by input received from the thermocouple 302 and the power decreased to the heating coils as necessary to maintain the temperature of the exiting gas flow. Once the gas flow has reached the operating flow rate and temperature, the stents are moved into the drying area 363. The stents are rotated by a rotation mechanism built into the spindle assembly 360. After drying is complete the gas flow is again returned to the idle position and the power to the heating coils increased as necessary to maintain the same gas flow temperature (based on input received from the thermocouple 302). The process repeats until the desired coating weight is obtained.

Reflector and Expander Embodiments

According to another aspect of the disclosure a dryer includes structure external to the dryer nozzle exit 3 to control or effect the interaction between ambient air and gas exiting the dryer and surrounding the stent. As will be appreciated, when gas exits the nozzle at high velocities there is a corresponding drop in pressure, which causes the ambient air to be drawn in towards the nozzle exit and stent surface and mix with the hot gas. As a result, the cooler ambient air draws heat away from the hot gas exiting the nozzle and reduces the efficiency of the hot gas to remove solvent.

In one embodiment, a dryer is configured in combination with a reflector to redirect or focus gas passing by the stent S back towards the stent to increase the efficiency of the hot gas to evaporate or boil off solvent from the stent surface. FIG. 5 illustrates the stent S disposed between a curved reflector 120, e.g., parabolic or semicircular, and the dryer 1, and the circulation of hot gas around the stent and reflected by the reflector surface 122. In the region between the reflector 120 and the stent S the gas pressure is increased. As a result, the cooler ambient air mixes less with the hot gas and draws less heat away from the gas passing by the stent.

In another embodiment, a gas expander 140 is fitted over the nozzle exit to shield or insulate the hot gas exiting from the dryer from the cooler ambient air, as depicted in FIG. 6. As the gas exits the nozzle it expands as it travels through the expansion space formed by expander 140. This increases the gas pressure surrounding the stent, thereby causing less heat loss before the gas reaches the stent surface. The higher pressure also serves to maintain the uniformity of gas in the vicinity of the stent. This is depicted in FIG. 6 by the turbulent mixture of ambient air and hot gas that forms in areas away from the stent surface. The stent may be placed near, partially within or fully within the expander 140.

In some embodiments the gas expander may be sized based on the diameter of the stent, as depicted in FIG. 6. The stent's diameter D is shown. The width of the mouth, and height of the expander section are both 4D, or about four times the stent diameter. And the stent is sunken into the expansion chamber by about 1 D, as illustrated. In other embodiments the mouth may be less than 4D while the height is the same. In one embodiment, the mouth is 2D while the height is 4D. It is believed that the more narrow mouth according to this embodiment will produce a more uniform gas temperature and velocity about the stent, while making the placement within the expander during a high volume coating/drying process easy to implement, or without other drawbacks resulting from a more narrow mouth, as will be appreciated. preferably, however, the mouth diameter is 4D.

In some embodiments the stent may be placed closer, or further from the nozzle exit 3. If the stent is placed too close to the nozzle exit 3, the distance between the leading edge of the stent and exit may create an uneven flow condition, which can cause the stent to be jostled about. In other embodiments the stent may be moved further than 3D from the nozzle but within the mouth. A stent placed outside of the mouth may not benefit as much from the environment provided by the gas expander. In those cases the ambient air may interfere with the velocity and temperature near the stent surface, thereby producing more unpredictable results or loss of drying efficiency. It is believed that an optimal efficiency and uniformity may be achieved when the stent is placed 1D within the mouth, 3D from the nozzle, and the gas expander mouth and height are respectively, 4D and 4D. In some embodiments the stent is placed at 75% of the mouth distance from the nozzle and the ratio of width to height is 1:1. It was found that with this condition, uniformity of solvent removal was maintained, or indeed improved and efficiency of solvent removal improved. Further, as mentioned earlier, in some embodiments the optimal distance may be found from the solution to the optimization constrained by three variables: (1) expander design, (2) heat transfer associated with gas and surrounding environment and (3) the type of stent support used.

Spray Nozzle

According to another aspect of the disclosure a spray nozzle is manufactured to reduce clogging and improve consistency of a drug-polymer dissolved in a solvent.

Figure 9:
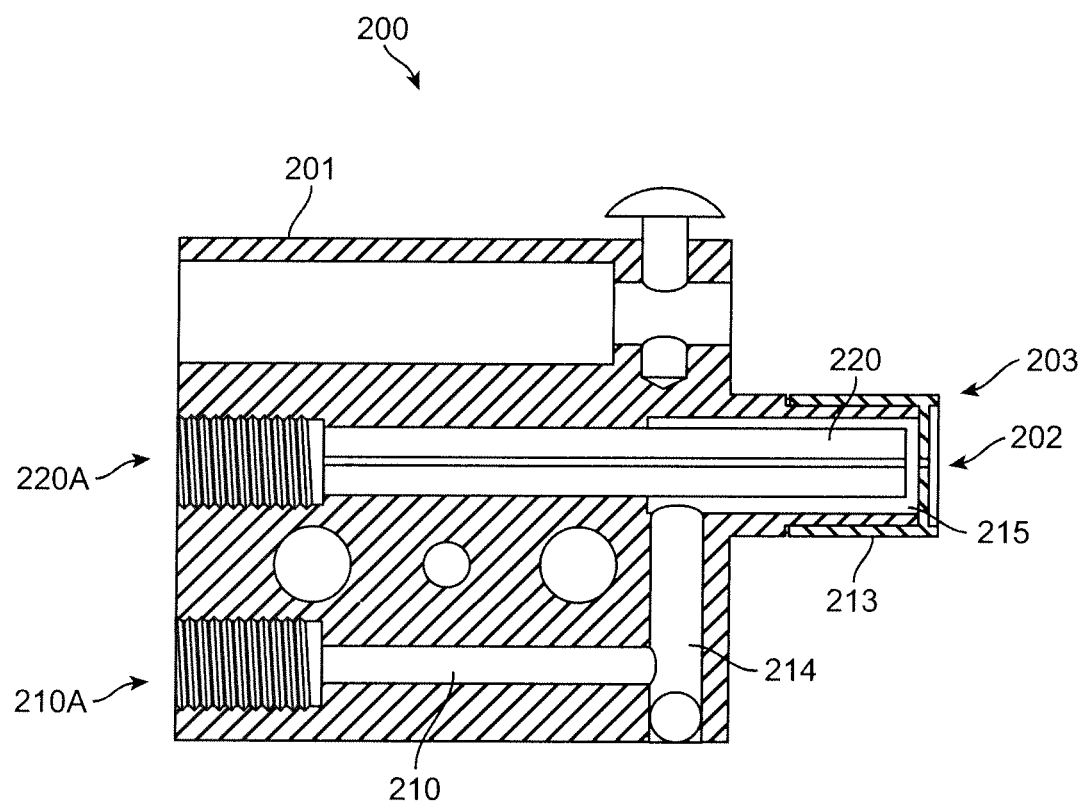
FIG. 9 is a prior art spray nozzle. The spray nozzle of FIGS. 8A-8C is an improvement over the spray nozzle of this figure. The spray nozzle of FIG. 8 produces a more consistent atomized stream of a drug-polymer-solvent, and has less clogging than the prior art nozzle of FIG. 9.

Referring to FIG. 9, a prior art spray nozzle 200 is shown. The nozzle 200 is an atomizing spray nozzle that may be used to produce a conical spray pattern of an atomized solution of a fluid. The nozzle may use a constant airflow with pulsed delivery to produce the atomized spray pattern. A prior art spray nozzle suitable for this use is the Sonicair™ nozzle available from the IVEK Corporation™, 10 Fairbanks Rd. North Springfield, Vt. 05150 USA.

The nozzle 200 includes a housing 201 having a first bore formed to receive a cannulae 220, which carries the fluid to the nozzle tip 203, and a third and fourth bore 210 and 214 which provides a conduit for pressurized gas used to atomize the fluid at the tip 203. A threading is provided at the opposite end for connecting a liquid supply line 220A and gas supply line 210A.

At the exit 203 a nozzle cap 213 having a centrally located orifice, sized according to the desired droplet size in the spray pattern, is placed over the exit hole 202 of the cannulae 220, which is in fluid communication with a chamber 215 in fluid communication with pressurized gas conduits 210, 214.

It was discovered that drug-polymer coatings applied using the nozzle 200 produced unacceptable variations in spray patterns and frequent clogging. Certain modifications (as described below) were made to the nozzle in the hopes that these problems could be eliminated.

Surprisingly and unexpectedly, it was found that a much improved spray pattern and less frequent clogging occurred when these modifications were implemented.

When it was discovered that the coating process could be significantly improved overall by improving upon the nozzle, attempts were made to improve on the existing prior art nozzle by polishing interior and exterior surfaces proximal the nozzle orifice. It was discovered during tests using a particular polymer-drug-solvent solution, e.g., 93% solvent and 7% drug-polymer, and desired conical spray pattern that the exiting prior art nozzle contained several shortcomings. In short, for the particular application of a drug-polymer coating according to one aspect of the invention it was discovered that the commercial nozzle, an example of which is provided here, although designed to produce precise and consistent spray patterns for applying a drug-eluting coating to medical devices and, in particular, stents, fell well short of the requirements for a drug-eluting coating having the required tolerance in the coating weight and distribution needed to achieve the objects of the disclosure, as previously discussed.

Two aspects of the nozzle that were found to produce inconsistent results were manufacture by an EDM process and nozzle-to-nozzle variations due to tolerances for parts during manufacture being too large. Polishing inner and outer areas proximal the nozzle orifice, for example, was not enough by itself to solve the problems. Nor was switching to a different design of sprayer. For example, an ultrasonic-type nozzle was tested. This alternative did not improve results as non-uniform and inconsistent coatings were found on a stent sprayed using an ultrasonic-type nozzle.

Figure 8A:
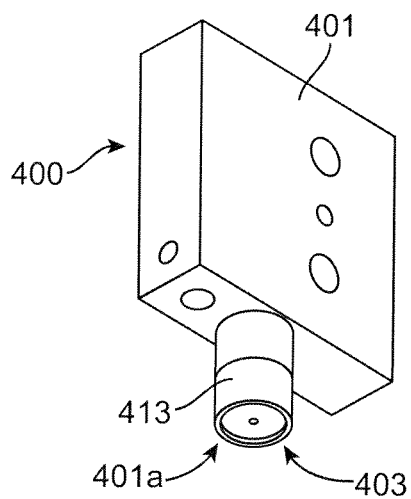
FIGS. 8A-8C are perspective, side and a cross-sectional view of a spray nozzle according to another aspect of the disclosure. The cross-sectional view is taken at section 8B-8B in FIG. 8C.
Figure 8C:
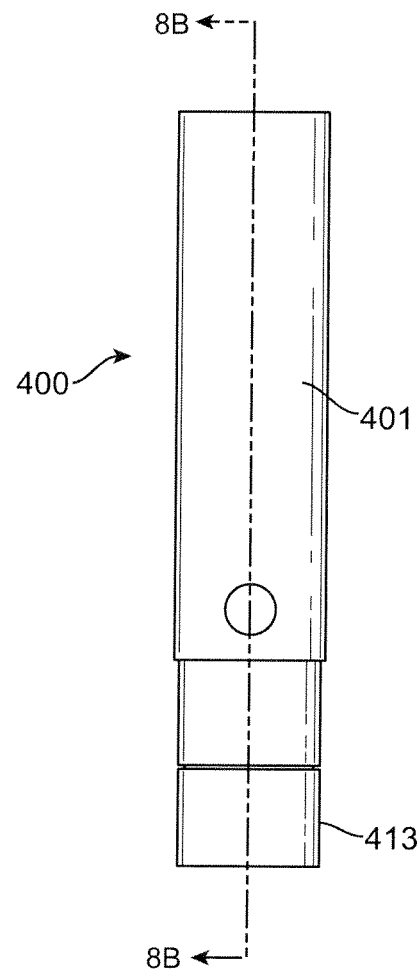
Figure 8B:
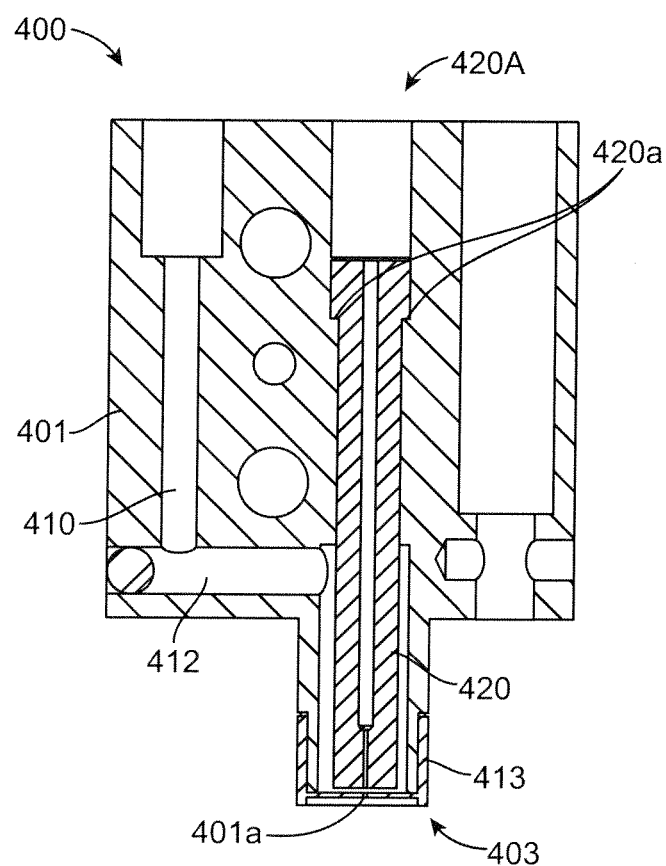

FIG. 8A illustrates a perspective view of an improved spray nozzle 400 according to the disclosure. FIG. 8C shows a side view of this nozzle and FIG. 8B shows a cross-sectional view of the nozzle 400 taken at section 8B-8B of FIG. 8C. The nozzle has a housing 401 which has a modified bore for receiving a modified cannulae 420, bores 410, 412 for passage of pressurized air and an exit end 403. A nozzle cap 413 is located at the nozzle end 403. The atomized drug-polymer-solvent solution exits from a modified orifice 401a.

Some of the important features of the nozzle of FIG. 8 that differ from the prior art nozzle of FIG. 9 are the finishing on the fluid surfaces, material, smoothness and consistency of the orifice hole and tight tolerances enforced in the nozzle passages.

The first improvement was in the use of different material. The housing 401 is made from 17-4 PH 900 heat treated steel whereas the cannulae 420 is made from 316 stainless steel. The nozzle 200, in contrast, is made from 316 stainless steel throughout. By using different materials in nozzle 400 having a different hardness, there is a tighter control of the press fit between the cannulae 420 and housing 401. Moreover, galling between the housing 401 and cannulae 420 is eliminated due to the different material, i.e., the 316 steel being a softer metal than the 17-4 PH 900 heat treated steel.

The second improvement was in the formation of the orifice of the end cap. The nozzle 200 end cap 213 is formed by a standard edge break on the inside and outside edges of the tapered orifice. This produced machining marks and variations around the orifice contributing to an inconsistent spray pattern (a result of an EDM manufacturing process). The end cap 413 for the nozzle 400 was instead made with more precise tolerance control. Additionally, surfaces on the inside and outside of the orifice were polished to produce more uniform surfaces for passage of the atomized fluid through the orifice (the end of the cannulae facing the orifice was also polished). These improvements in the nozzle cap 413 reduced instances of clogging, and produced a more uniform spray pattern as compared to the nozzle 200 end cap 213.

A third improvement was made in the cannulae. First, the cannulae was made with a stepped outer diameter for precise placement against a ledge 420A formed in the receiving bore of the housing. Mating with a stepped diameter bore also prevented the cannulae 420 from being pushed into the end cap 413 when the fluid supply fitting is secured at the connection 420A. The cannulae 220, by contrast, is formed as a constant diameter cylinder and received in a corresponding constant diameter bore. This assembly makes placement of the cannulae 220 within the bore less precise and the fit less snug.

Second, the cannulae 420 bore is made larger and steps down to a smaller diameter bore, which reduces the pressure drop along the length of the cannulae 420. The cannulae 220 of the nozzle 200 has instead a constant bore. By reducing the pressure drop there is a more consistent supply of fluid at the desired pressure, which contributes to a more consistent spray pattern.

A fourth improvement in nozzle performance relates to a method of reducing instances of clogging, particular between spraying intervals, i.e., when the stent is moved to the dryer. A buildup prevention method for a nozzle includes a secondary nozzle having its nozzle orientated towards, and at an angle of about 20-40 degrees relative to the nozzle cap 413 lower face. This nozzle delivers a steady stream of gas, e.g., Nitrogen gas, towards the orifice 401a between each spraying step. By applying this steady stream of gas a buildup of drug-polymer solution is forcibly blown off the orifice of the spray nozzle as the nozzle rests between spray cycles. Simultaneous with this applied gas is a sufficiently high pressure being maintained through the atomizing gas pressure source. This should prevent any buildup of drug-polymer solution from being blown into the bore of the cannulae 422 due to the secondary nozzle drying gas. In one embodiment, the 20-40 orientated drying gas was delivered at an exit pressure of 5-20 psi for about 1-3 seconds. The balancing pressure of the atomizing gas may be the same as the operating pressure, e.g., the recommended operating pressure for the Sonicair™ nozzle. According to this aspect of the disclosure, a stent drying and spraying process includes a spray nozzle drying step intermittent to spraying steps.

Although the above embodiments have been described in connection with a stent, it is to be understood that the present invention can be applied to devices other than stents. Medical devices to which this invention may be adapted for use includes balloon expandable stents, self-expanding stents, grafts, stent-grafts, balloons, and catheters.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A dryer having an inlet conduit supplying an incoming gas stream and an exit area that produces a drying gas, comprising:
    a first gas conditioning chamber and a second gas conditioning chamber together forming a closed space for the conditioning of a gas supplied by a gas source and discharged at a nozzle exit, the gas having a mass flow rate that is the same at the nozzle exit as the mass flow rate supplied by the gas source during a steady state flow condition;
    the first gas conditioning chamber including a circular inlet coupled to the gas source and a linear array of apertures downstream of the circular inlet; and
    the second gas conditioning chamber including the linear array of apertures and a linear array of nozzle exit channels downstream of the linear array of apertures;
    wherein the dryer is adapted for producing a substantially uniform drying air mass from the linear array of nozzle exit channels.

2. The dryer of claim 1, wherein the circular inlet has a diameter, the array of nozzle exit channels extends over a nozzle length, the inlet is spaced from the linear array of nozzle exit channels by a first length spanning both the first and second gas conditioning chamber, and the central axis of the circular inlet is separated from the nozzle exit, formed by the linear array of nozzle exit channels by a second length, wherein
    a nozzle length of the nozzle exit is at least five times larger than the inlet diameter,
    the nozzle length is at least twice as large as either the first length or the second length, and
    the dryer as adapted for producing a substantially uniform drying air mass over the linear array of nozzle exit channels at the rate of 100 standard liters/minute nitrogen gas at a temperature of approximately 100 to 120 degrees C.

3. The dryer of claim 2, wherein the dryer configured such that gas entering the circular inlet has a first mean flow direction, the gas entering the first gas conditioning chamber has a second mean flow direction, and the gas exiting the dryer from the linear array of nozzle exit channels has a third mean flow direction, wherein
    the first mean flow direction is perpendicular to the second mean flow direction and the third mean flow direction is perpendicular to the second mean flow direction and the first mean flow directions.

4. The dryer of claim 3, wherein first gas conditioning chamber is further configured such that gas has the third mean flow direction before the second mean flow direction.

5. The dryer of claim 4, wherein the linear array of apertures are configured such that the gas has the first mean flow direction when it leaves the first gas conditioning chamber and enters the second gas conditioning chamber.

6. The dryer of claim 1, wherein a mean flow direction through the circular inlet is perpendicular to a mean flow direction for gas within the first gas conditioning chamber.

7. The dryer of claim 6, wherein the first gas conditioning chamber includes a first section including a circular opening, a wall opposite the circular opening and three adjoining walls such that the gas is forced to make a right angle turn upwards when it enters the first section.

8. The dryer of claim 7, wherein the first gas conditioning chamber includes a second section having a side including an opening for receiving the gas from the first section, the side forming a portion of a cavity that extends lengthwise and parallel to the linear array of apertures, the linear array of apertures forming one of the walls and running parallel to the second section and the linear array of nozzle exit channels.

9. The dryer of claim 8, wherein the first gas conditioning chamber is T-shaped.

10. The dryer of claim 9, wherein a largest length of the T-shaped section is about the same length as the length spanned by the linear array of nozzle exit channels.

11. The dryer of claim 1, wherein the second gas conditioning chamber has an upstream portion and a downstream portion, and an intermediate portion between the upstream and downstream portions, the intermediate portion being tapered so that flow there through is accelerated before reaching the downstream portion.

12. The dryer of claim 11, wherein the second gas conditioning chamber has a mean flow direction that is perpendicular to a mean flow direction for gas supplied through the circular inlet.

13. The dryer of claim 1, wherein turbulence and noise-reducing vanes are formed at upstream ends of the linear array of nozzle exit channels.

14. The dryer of claim 13, wherein the linear array of nozzle exit channels form square openings.

15. The dryer of claim 13, wherein the linear array of nozzle exit channels are configured such that gas passing through the channels and exiting from the nozzle is substantially laminar flow.

16. The dryer of claim 13, wherein the noise reducing vanes are adapted for reducing the amplitude or degree of fluid oscillations at the nozzle exit.

17. The dryer of claim 1, further including a gas expander disposed about the linear array of channels.

18. The dryer of claim 17, the gas expander including a parabolic or conical skirt that diverges outwardly from the nozzle exit such that the hot gas is segregated from the surrounding ambient gas as it travels through the parabolic or conical skirt.

19. The dryer of claim 18, the gas expander being configured for insulating exit gases from ambient air until the pressure of the gas builds up sufficiently to minimize substantial heat loss near the nozzle exit.

20. The dryer of claim 1, further including a gas reflector disposed opposite the linear array of nozzle exit channels.

21. The dryer of claim 20, wherein the reflector is a semicircular or parabolic surface configured for forming a high pressure region of hot gas for a stent disposed between the reflector and nozzle exit.

22. The dryer of claim 1, wherein the ratio of the total flux area for the linear array of apertures to the linear array of nozzle exit channels is about 4:1.

23. The dryer of claim 1, wherein the ratio of the total flux area for the linear array of apertures to the circular inlet may be about 1.75:1 or 2:1.

24. The dryer of claim 1, wherein the ratio of the total flux area for the nozzle exit channels to the circular inlet flux area is about 2:1.

25. The dryer of claim 1, wherein the array of nozzle exit channels have a length L, the depth of the combined chambers between inlet and exit is D, the height of the combined chambers between inlet and exit is H and the size of the diameter at the inlet is 2R, wherein the ratio of L to D, to H to 2R (L:D:H:2R) is about 1:(1/10):(1/3):(1/8);

the ratio of L:2R is about 1:8;

the ratio of L:D is about 1:1/10; or the ratio of L:H is about 1:1/3; and wherein the dryer is capable of producing a uniform temperature and velocity suitable for drying a stent for a flow rate of about 100 liters/min at a temperature in the range of 100 to 120 degrees Celsius.

26. The dryer of claim 1, wherein a length of the linear array of nozzle exit channels is about 125% of the length of a stent, or 1.5 times the length of a stent length for which the dryer is configured for drying to produce a uniform heat transfer from the gas to the stent surface.

27. The dryer of claim 17, wherein the gas expander is sized such that it has a height, mouth, or depth of insertion of a stent size that is about a multiple of the diameter of the stent.

28. The dryer of claim 27, wherein the gas expander is configured for maintaining a uniform heat transfer near the stent surface, the stent having a diameter D, wherein the height of the expander is about four times D, the mouth of the diameter is between two times and four times D, and the stent is placed about a D distance from the mouth.

29. The apparatus of claim 1, further including a gas expander having a height to mouth ratio of 1:1.

* * * * *